(12) United States Patent
Chatenever

(10) Patent No.: US 6,511,422 B1
(45) Date of Patent: Jan. 28, 2003

(54) METHOD AND APPARATUS FOR PROTECTION FROM HIGH INTENSITY LIGHT

(75) Inventor: David Chatenever, Santa Barbara, CA (US)

(73) Assignee: Karl Storz Imaging, Inc., Goleta, CA (US)

(*) Notice: Subject to any disclaimer, the term of this patent is extended or adjusted under 35 U.S.C. 154(b) by 0 days.

(21) Appl. No.: 10/135,318

(22) Filed: Apr. 30, 2002

(51) Int. Cl.⁷ ................................................. A61B 1/06
(52) U.S. Cl. ...................................................... 600/180
(58) Field of Search .................. 600/118, 178–182; 348/68–70; 362/574, 276; 606/11, 12, 14–16; 607/89; 214/121.62

(56) References Cited

U.S. PATENT DOCUMENTS

| | | |
|---|---|---|
| 3,670,722 A | 6/1972 | Kosaka |
| 4,325,618 A | 4/1982 | Hosoda |
| 4,527,552 A | 7/1985 | Hattori |
| 4,561,429 A | 12/1985 | Sato et al. |
| 4,963,960 A | 10/1990 | Takami |
| 5,131,381 A | 7/1992 | Ams et al. |
| 5,134,469 A | 7/1992 | Uchimura |
| 5,154,707 A * | 10/1992 | Rink et al. ............... 606/12 |
| 5,159,380 A | 10/1992 | Furuya et al. |
| 5,162,913 A | 11/1992 | Chatenever et al. |
| 5,374,953 A * | 12/1994 | Sasaki et al. ............. 348/65 |
| 5,957,834 A | 9/1999 | Mochida |
| 6,468,204 B2 * | 10/2002 | Sendai et al. ............. 600/178 |

FOREIGN PATENT DOCUMENTS

JP 62155689 10/1987

* cited by examiner

Primary Examiner—John Mulcahy
(74) Attorney, Agent, or Firm—St. Onge Steward Johnston & Reens LLC

(57) ABSTRACT

A method and apparatus where the output from a high intensity light source is controlled so that whenever the output is not directed at a surface, the light source output intensity is automatically reduced to a safe level. This is achieved by monitoring the reflected light from a surface and when this reflection indicates that the light source is not directed at a surface, the light intensity is reduced to a safe level.

13 Claims, 3 Drawing Sheets

METHOD AND APPARATUS FOR PROTECTION FROM HIGH INTENSITY LIGHT

FIELD OF THE INVENTION

This invention generally relates to a method and apparatus for automatically protecting personnel from direct exposure to the output of a high intensity light source. More specifically, this invention relates to a method and apparatus for protecting the eyes from direct exposure to high intensity light used in medical devices such as endoscopes and the like. Additionally, the risk of inadvertent ignition of combustible material, such as paper surgical drapes, caused by close proximity to high intensity light source outputs, is avoided.

BACKGROUND OF THE INVENTION

The imaging of body surfaces through an endoscope is well known within the medical and veterinarian fields. Typically, this involves inserting an endoscope into a body cavity and directing an intense light source output through the endoscope to illuminate body tissue. Light reflected by the body tissue then is guided along an optical path to an image sensor to generate a video image of the tissue. One such approach is described in U.S. Pat. No. 5,162,913 to Chatenever, et al, and provides a technique for an automatic adjustment of the exposure of video images detected with a CCD (charge coupled device) image sensor.

The use of high intensity light sources involves potential hazards to medical personnel and patients. For example, when a light guide cable, used to convey the intense light source output, is momentarily disconnected from the endoscope and placed on a sterile drape used to protect the patient, the light output intensity can be sufficient to ignite the drape and pose a fire hazard; or, the user can inadvertently hold the disconnected light guide cable in such a way as to temporarily blind another person in the room. In some instances, when the endoscope is pulled out of a patient, there can be a risk of these same hazards. When the light source is used with an endoscopic video camera, which has an automatic exposure system, the light source may be turned up to an intensity level higher than required for the camera to produce well-exposed images. This increased light intensity level can desiccate body tissue and cause serious injury to the patient. Typically, endoscopic video camera automatic exposure systems can produce well-exposed images with an electronic shutter setting of approximately $1/125^{th}$ to $1/500^{th}$ of a second. If an endoscope distal end is placed within close proximity to tissue being imaged, typically, a relatively low light intensity level will still enable an endoscopic video camera to produce well-exposed images. An undesirable, and potentially dangerous, scenario can occur if the light source output is set to a high level, and the endoscope distal end is placed within close proximity to tissue being imaged. Typically, in such a case, camera automatic exposure systems will adjust electronic shutter settings to approximately $1/10,000^{th}$ of a second (or faster) to compensate for the high illumination reflections from the tissue. In such a situation, the risk of desiccating delicate tissue is greatly increased.

A technique for automatically controlling the light intensity from a light source, on the basis of an image signal from an imaging unit associated with an endoscope, is described in Japanese Unexamined Patent Publication No. 62-155689 as mentioned at column 2, lines 1–21 in U.S. Pat. No. 5,957,834 to A. Mochida. As recognized in the Mochida patent, when light intensity control is made dependent upon a signal derived from the image, then upon removal of the endoscope from the body, the control is likely to increase the intensity level from the light source, when instead it should decrease it to protect the operator's eyes from accidental exposure and prevent ignition of combustible material. In the Mochida patent a switch is added to manually adjust and control the output of the light source when the endoscope is removed from a body.

As further described in the Mochida patent the intensity level of the light source is controlled by regulating the position of a diaphragm with respect to the light source. The control signal for doing this is derived from an image sensor in the endoscope.

In U.S. Pat. No. 4,527,552 a photoelectric element generates a signal indicative of the intensity of light reflected from an object illuminated by a light source associated with the endoscope to control the light source output level. In U.S. Pat. No. 5,131,381 a light source associated with an endoscope is controlled by a signal that represents the density value of each line of a camera video image derived through the endoscope. Other patents relevant to light intensity level controls for endoscopes are U.S. Pat. Nos. 5,159,380; 3,670,722; 5,134,469; 4,963,960; and 4,561,429.

Techniques have been proposed to reduce the risks associated with high intensity light sources. One involves a special light guide cable with wires in it that are shorted together when the cable is attached to an endoscope. The short is detected at the light source and light intensity is reduced when the cable is disconnected and the short is subsequently removed. A retractable mechanical shroud, which covers the light guide when not connected to an endoscope, has also been suggested.

These safety solutions are not necessarily effective against all potential hazardous conditions that may arise; such as when the endoscope with the light guide cable still attached is pulled out of a patient and inadvertently directed at a person or surgical drape, or when the light guide or source initially is directed to treat openly accessible tissue and inadvertently misdirected during or after a procedure, or when a video camera head, attached to the endoscope light guide cable combination, is disconnected from its corresponding control unit.

SUMMARY OF THE INVENTION

With a method and apparatus, in accordance with the invention, the output from a high intensity light source is controlled so that whenever the output is not directed at tissue (meaning that the endoscope/video camera/light source combination is not currently being used to image body tissue), the light source output intensity is automatically reduced to a safe level. This is achieved by monitoring the reflected light from tissue and when this reflection indicates that the light source is not directed at tissue, the light intensity is turned down to a safe level.

As described herein for one preferred form of the invention, the light source is provided with a characteristic signal. The absence of this characteristic signal from reflected light becomes indicative that the light source is not directed at tissue and the light intensity needs to be reduced to avoid inadvertent light related injury. This characteristic signal can be a frequency or wavelength modulation, but preferably is an amplitude or intensity modulation at a distinctive frequency so that the modulation can be detected in reflected light.

In one embodiment, in accordance with the invention, a modulation signal is generated and is superimposed on the high intensity light source output. The light source output thus includes a modulation signal that is also present in reflected light, which can be detected by a video camera imager. The lack of detection of the modulation signal can then be used to indicate when the light source output is not directed at tissue, thus initiating a dramatic reduction in light intensity.

The technique of this invention can be particularly effective in assuring protective control over a high intensity light source used as part of an endoscopic video system utilizing a communication bus to interconnect various devices. In such case, the light source modulation is extracted from the pixel signals at the output of an endoscopic image sensor used to detect light reflected from tissue observed through an endoscope. As long as this modulation signal is detected, the high intensity light source output remains at a level adequate to produce well-exposed video images. However, once the modulation signal either disappears or drops below a specific reference level, it is assumed that the light guide cable is no longer attached to the endoscope, or that the endoscope itself is removed from the patient, and a protective reaction is initiated. The loss or reduction of the modulation signal is thus converted to a control signal that is sent by means of the bus to the light source, causing the output intensity to be turned down to a safe level.

Additionally, as described herein, a method is provided, by the invention, to determine when the light source output exceeds a level necessary for an endoscopic video camera to produce well-exposed images.

It is, therefore, an object of the invention to provide a method and apparatus with which automatic protection of personnel against accidental exposure to high intensity light from a light guide cable, used with or without an endoscope attached, is obtained.

It is a further object of the invention to provide a video camera/light source control for an enhanced safety of the use of an endoscope using the high intensity light source for the illumination of tissue.

It is still further an object of the invention to provide a control over the overall light output from a high intensity light source used to illuminate an object observed through an endoscope.

These and other objects of the invention can be understood from the following detailed description of a preferred embodiment of the invention in conjunction with the drawings.

DETAILED DESCRIPTION OF THE DRAWINGS

Figure 1:
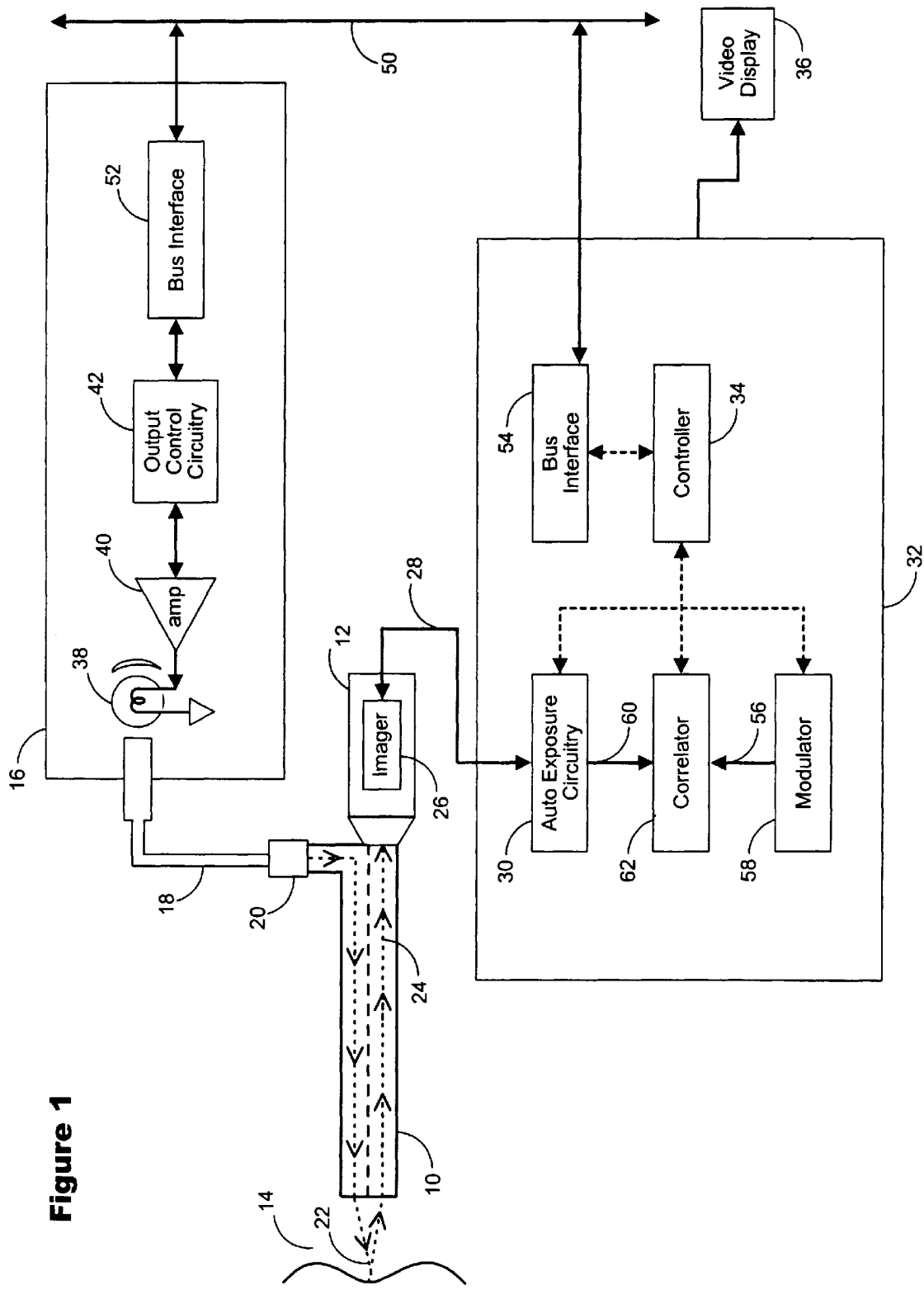
FIG. 1 is a schematic block diagram view of an apparatus for controlling a light source in a safe manner in accordance with the invention.

With reference to FIG. 1, a typical endoscope 10 is illustrated having a camera head 12 mounted thereto at the proximal end to produce video images in a manner for example as described in the aforementioned '913 patent. The distal end of endoscope 10 is directed at tissue 14 to inspect the tissue with light from a high intensity light source 16 and passed to the distal end through a light guide cable 18. Typically, light guide cable 18 can be disconnected from endoscope 10 at connector 20, thus, posing a safety hazard as previously described.

The light from light guide cable 20 is directed to illuminate tissue 14 as suggested with path 22 and light reflected by tissue 14 is passed along optical path 24 to imager 26 within camera head 12. Imager 26 detects light reflected off tissue 14 by means of optical path 24. Imager 26 may be any type commonly used within the art, such as but not limited to CCD, CID or CMOS imagers. Camera head 12 produces image signals 28, which are received by auto exposure circuitry 30, within camera control unit (CCU) 32. Auto exposure circuitry 30 may consist of various types of methods for controlling the electronic shutter of imager 26, as well as adjusting amplification gain in response to illumination levels received by imager 26. Typically, within the field of video endoscopy, auto exposure circuitry has high-speed and wide dynamic range capabilities. Various methods may be utilized, that are well known within the art. Video display 36, receives signals from CCU 32, where an image of tissue 14 is presented.

In the embodiment of FIG. 1, light source 16 is controlled by CCU 32 controller 34, by means of CCU bus interface 54, digital communication bus 50, and light source bus interface 52. Controller 34, may be any type of device designed to receive and execute software programs, or which is designed to be modified in functionality by software programs, and preferably is from the group consisting of digital signal processors, microcontrollers, and microprocessors, or the group consisting of field programmable gate arrays, and computer programmable logic devices.

Typically, high intensity light sources utilize an incandescent bulb 38 (being a xenon bulb, or other type), driven by an amplifier 40, which in turn is controlled by output control circuitry 42, to set the light intensity level of the light source 16. Other types of light source intensity output control are known within the art; such as mechanical diaphragm or iris, liquid crystal shutter, rotary reed or slot devices, and the like. These various types of light source output control may be utilized within the scope of the present invention. In the present embodiment, output control circuitry 42 varies the intensity of bulb 38 in accordance with a "slow" time varying signal 56 output from modulator 58 (within CCU 32) by means of CCU bus interface 54, bus 50, and light source bus interface 52, under the control of controller 34. What is meant by "'slow' time varying signal" is that, preferably, signal 56, is of the order of approximately two to four seconds per cycle (well below the response time of auto exposure circuitry 30). Also, "slow" time varying signal 56 is of an amplitude level that produces about a 5% to 10% modulation (change in intensity) of the maximum output intensity of light source 16. Therefore, CCU 32 can control the overall light output level of light source 16, and CCU 32 can also vary the set overall light output level in accordance with "slow" time varying signal 56, both in rate and intensity amplitude.

Light reflected from tissue 14 contains the amplitude (intensity) modulation, which is detected by imager 26, and is present in video data on line 28. Auto exposure circuitry 30 not only adjusts the camera exposure to produce an optimized video image, but also, as part of this exposure adjustment, compensates for the intensity modulation (driven by modulator 58 "slow" time varying signal 56). Due to the modulation's "slow" rate and "low" amplitude, auto exposure circuitry 30 easily compensates for the varying light level, and thus the change in light amplitude is not perceived by viewer's of video monitor 36.

Auto exposure circuitry 30 outputs detected modulation signal 60, which retains data corresponding to the intensity modulation. Detected modulation signal 60 is received by correlator 62. Correlator 62 also receives "slow" time varying signal 56 from modulator 58.

Figure 2:
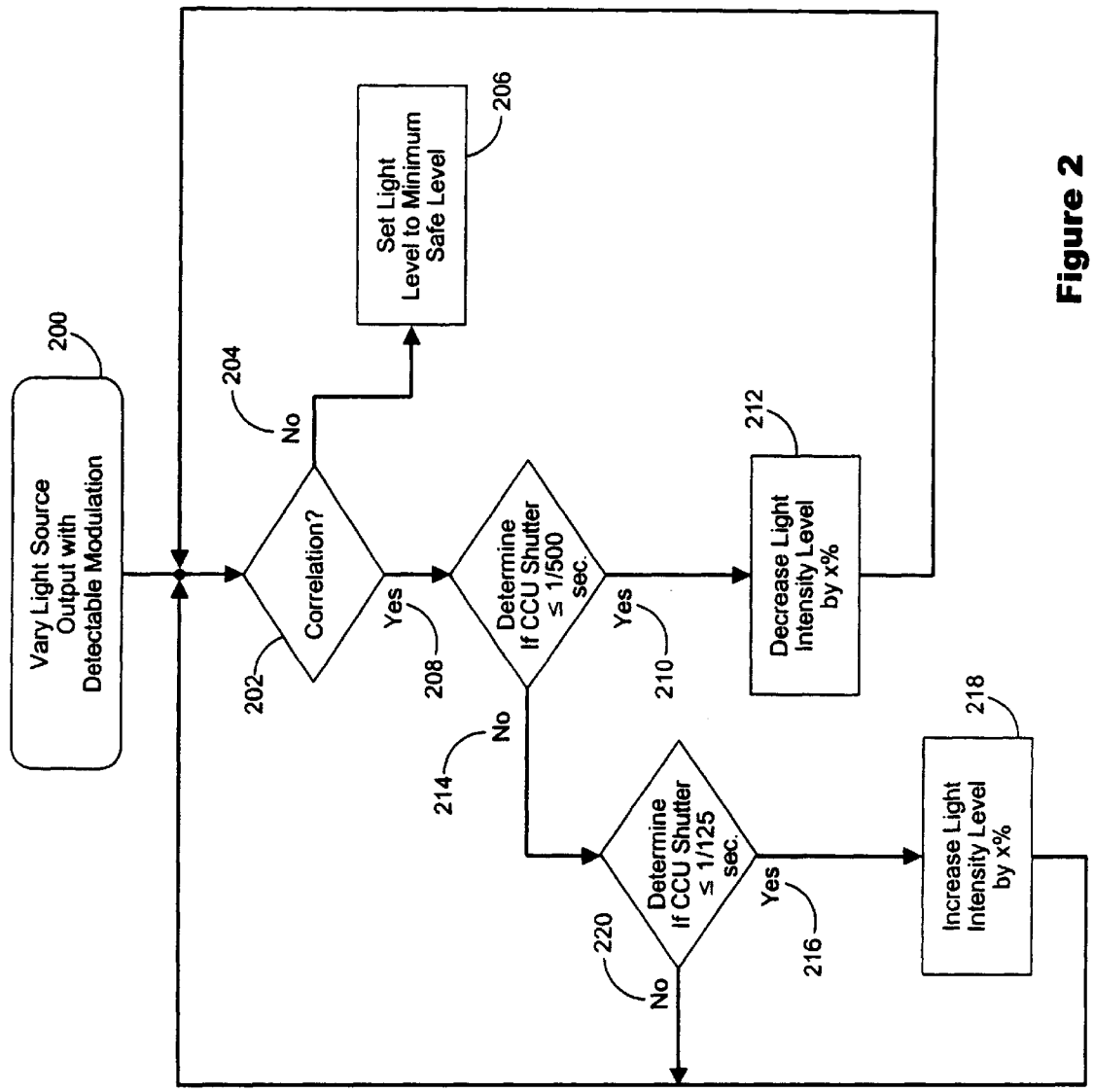
FIG. 2 is a flow diagram for controlling a high intensity light source to reduce risk of injury to personnel; and for optimizing the overall output level of a high intensity light source, when used to illuminate target tissue with an endoscope and endoscopic video camera system.

FIG. 2 is a flow diagram for a method of controlling a high intensity light source to reduce risk of injury to personnel; and for optimizing the overall output level of a high intensity light source, when used to illuminate target tissue with an endoscope and endoscopic video camera system. The light source output is varied 200 in accordance with "slow" time varying signal 56 output by modulator 58, as previously described. Detected modulation signal 60 and "slow" time varying signal 56 are compared for correlation 202. If the two modulation signals (60, 56) do not correlate 204 (i.e. the modulation is not detected by auto exposure circuitry 30), controller 34, by means of CCU bus interface 54, bus 50, light source bus interface 52, and output control circuitry 42, reduces the light source intensity level to a minimum safe level 206. What is meant by "minimum safe level" is that the light source output is reduced to a level where the modulation signal can be detected when a condition causing non-correlation is corrected (i.e. the light intensity is at its lowest level in which the modulation signal can still be detected, within the light source output, by auto exposure circuitry 30). Some conditions which cause non-correlation 204 are: the light guide cable 18 being disconnect from light source 16 or endoscope 10, the camera head 12 being disengaged from endoscope 10, or the light guide cable/camera head/endoscope combination being removed from a patient (thus, light is not reflected off body tissue).

If the two modulation signals (60, 56) do correlate 208 (i.e. the modulation is detected by auto exposure circuitry 30), to provide a control loop which sets the overall light source output 22 to an optimum level, the current CCU electronic shutter setting is checked. What is meant by "optimum level" is that the light source intensity is kept at the lowest possible level which produces a well-exposed video image from CCU 32. Typically, light source outputs are set manually by medical personnel, and CCU auto exposure circuitry adjusts imager electronic shutter and/or gain amplification levels to produce an acceptable image, with the existing manually set light intensity level.

As previously described, the light intensity level may be manually set much higher than is required for the CCU to produce well-exposed video images. After correlation has been established 208, in order to maintain the light source output intensity at a safe level, if the CCU electronic shutter is less than or equal to $1/500^{th}$ of a second 210, the light intensity level is decreased by a certain percentage 212 (of the total light source output capability). This control loop, 202, 208, 210, and 212 is repeated until the CCU electronic shutter is greater than $1/500^{th}$ of a second 214.

To ensure adequate light is present for the CCU to produce well-exposed video images, if the CCU electronic shutter is greater than $1/500^{th}$ of a second 214, and if the CCU electronic shutter is greater than or equal to $1/125^{th}$ of a second 216, the light source intensity level is increased by a certain percentage 218. This control loop, 202, 208, 214, 216, and 218 is repeated until the CCU electronic shutter is less than $1/125^{th}$ of a second 220. If the CCU electronic shutter is greater than $1/500^{th}$ of a second 214, and less than $1/125^{th}$ of a second (as depicted by loop 202, 208, 214, and 220) the light source output level is maintained at its current intensity level.

The percentage of light intensity increase or decrease will determine the speed at which the level is adjusted. Preferably, the percentage is relatively small (approximately 1% to 3% of the total light source capability), which will allow the light source output to slowly "creep" (within approximately 5 seconds) to an optimal intensity level.

Figure 3:
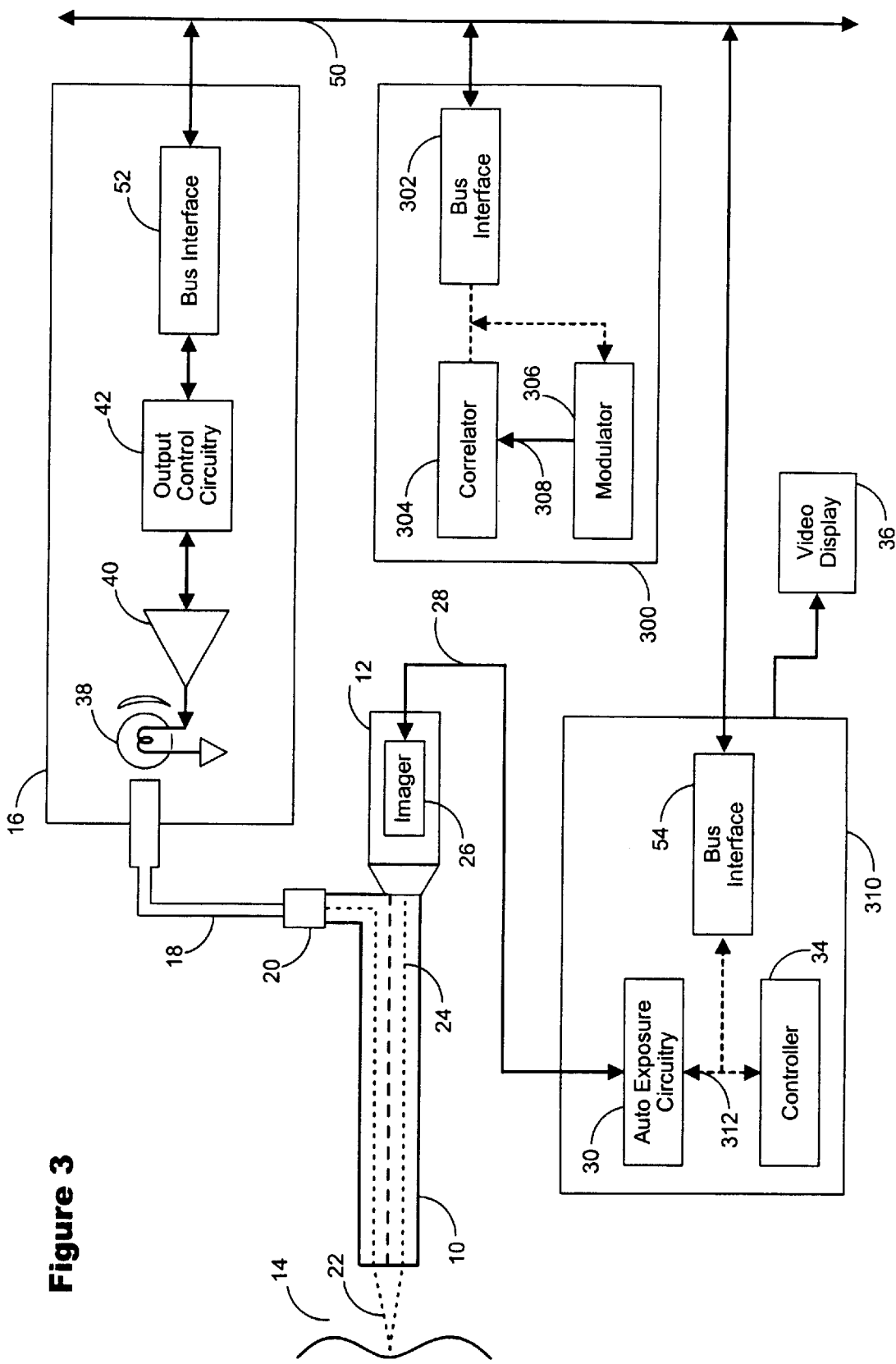
FIG. 3 is a schematic block diagram view of another apparatus for controlling a light source in a safe manner in accordance with the invention.

FIG. 3 depicts another embodiment of the present invention, in which correlator/modulator 300 is connected to bus 50, separate from CCU 310 and light source 16. Correlator/modulator 300 comprises, bus interface 302, correlator 304, and modulator 306. Within CCU 310, controller 34 still functions as described in the previous embodiment, except that control of correlator 304 and modulator 306 is accomplished by means of CCU bus interface 54, bus 50, and bus interface 302.

The present embodiment is identical to the previous embodiment with the following exceptions: light source 16 output control circuitry 42 varies the intensity of bulb 38 in accordance with a "slow" time varying signal 308 output from modulator 306 by means of commands routed from controller 34 to CCU bus interface 54, bus 50, bus interface 302, and light source bus interface 52. Auto exposure circuitry 30 outputs detected modulation data 312 (corresponding to the light level modulation) to bus 50 by means of bus interface 54, under control of controller 34. Detected modulation data 312 is received by correlator 304 via bus interface 302. Correlator 304 also receives "slow" time varying signal 308 from modulator 306. Steps to control light source 16, to reduce risk of injury to personnel; and for adjusting the average light output intensity, are identical as described for the previous embodiment, as detailed for FIG. 2.

Having thus described several embodiments for practicing the invention, its advantages and objects can be understood. Variations from the drawings and description can be made by one skilled in the art without departing from the scope of the invention, which is to be determined from the following claims. One example being that light source 16 and CCU 32 may be housed within a single housing, thus obviating bus 50, and bus interfaces 52 and 54.

What is claimed is:

1. A method for protecting personnel from an intense light source output used for the illumination of a surface observed through an endoscope, comprising the steps of:
   generating a modulation signal:
      modulating the intensity of the light source output with the modulation signal;
      monitoring light received along a light path in the endoscope from the surface illuminated by the light source output and detecting the modulation in the received light;
      reducing the intensity of the light source output to a selected level when the detected modulation is below a reference level; and
      adjusting the intensity of the light source output when the detected modulation is above the reference level;
      said adjusting of the intensity of the light source output based upon the exposure setting of an endoscopic video camera.

2. An apparatus for protecting personnel from direct illumination by an intense light source output used for the illumination of a surface observed through an endoscope, comprising:

an endoscope having an imaging path through which the surface at a distal end can be observed;

a light source for illumination of the surface;

a camera head including an image sensor aligned to detect light reflected from the surface and passed along the endoscope imaging path and for generating image signals;

a camera control unit for processing the image signals received from the camera head;

a modulator producing modulation signals utilized in varying the light source output intensity with a selected modulation;

a correlator receiving the image signals for determining the presence of the selected modulation within the image signals; and a communication bus coupled to a plurality of bus interfaces for communication between the light source, camera control unit, modulator, and correlator.

3. The apparatus of claim 2 wherein the camera control unit includes a first bus interface.

4. The apparatus of claim 2 wherein the light source includes a bus interface.

5. The apparatus of claim 2 wherein the camera control unit includes a controller associated with the camera head to process image signals representative of images detected by the image sensor, and coupled to the first bus interface.

6. The apparatus of claim 5 wherein the controller utilizes the modulation signals to produce light intensity output signals on the communication bus for varying the light intensity output of the light source.

7. The apparatus of claim 5 wherein the controller receives correlator data from the correlator and reduces the light source output intensity to a safe level if the correlator data indicates that the predetermined modulation contained within the image signals is below a predetermined reference level.

8. The apparatus of claim 2 wherein the modulator and correlator are within the camera control unit.

9. The apparatus of claim 2 wherein the modulator and correlator are within the light source.

10. The apparatus of claim 2 wherein the modulator is within the light source and the correlator is within camera control unit.

11. The apparatus of claim 2 wherein the modulator and correlator are remotely located and coupled to the communication bus via a bus interface.

12. An apparatus for protecting personnel from an intense light source output used for the illumination of a surface observed through an endoscope, comprising:

a light source having a light output with a selected modulation;

an image sensor associated with the endoscope for detecting light passed therethrough and reflected from the illuminated surface;

a correlator responsive to the output from the image sensor to produce a safety signal indicative of the modulation level of the light source output; and a controller responsive to the safety signal for reducing the intensity of the light source output to a selected level when the safety signal is indicative of the light source output modulation level being below a selected reference level.

13. A method for protecting personnel from an intense light source output directed at a surface, comprising the steps of:

generating a modulation signal:

modulating the output intensity of the light source with the modulation signal;

monitoring light reflected by the surface;

detecting the modulation in the monitored light; and reducing the intensity of the light source output when the detected modulation is below a reference level.

* * * * *